United States Patent
Monaghan et al.

(10) Patent No.: US 9,439,766 B2
(45) Date of Patent: Sep. 13, 2016

(54) MULTI-LAYERED PROSTHETIC CONSTRUCTS, KITS, AND METHODS

(71) Applicant: Zimmer, Inc., Warsaw, IN (US)

(72) Inventors: Matthew E. Monaghan, Fort Wayne, IN (US); David M Miller, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 172 days.

(21) Appl. No.: 13/867,564

(22) Filed: Apr. 22, 2013

(65) Prior Publication Data

US 2013/0282134 A1  Oct. 24, 2013

Related U.S. Application Data

(60) Provisional application No. 61/637,024, filed on Apr. 23, 2012.

(51) Int. Cl.
*A61F 2/36* (2006.01)
*A61F 2/38* (2006.01)
(Continued)

(52) U.S. Cl.
CPC ............... *A61F 2/30* (2013.01); *A61F 2/3609* (2013.01); *A61F 2/3859* (2013.01); *A61F 2/3094* (2013.01); *A61F 2002/30037* (2013.01); *A61F 2002/30077* (2013.01); *A61F 2002/30968* (2013.01); *A61F 2002/30971* (2013.01); *A61F 2310/00203* (2013.01); *A61F 2310/00215* (2013.01); *A61F 2310/00239* (2013.01);
(Continued)

(58) Field of Classification Search
CPC ............... A61F 2002/30037; A61F 2250/004; B29C 65/665

USPC ...................................... 623/23.56
See application file for complete search history.

(56) References Cited

U.S. PATENT DOCUMENTS

| | | |
|---|---|---|
| 3,673,049 A | 6/1972 | Giffen et al. |
| 3,849,097 A | 11/1974 | Giffen et al. |
| 4,103,002 A | 7/1978 | Hench et al. |

(Continued)

FOREIGN PATENT DOCUMENTS

JP        10-328292 A  * 12/1998  ............. A61L 27/00

OTHER PUBLICATIONS

EPO computer translation of JP 10-328292 A, originally published on Dec. 15, 1998.*

(Continued)

*Primary Examiner* — David H Willse
(74) *Attorney, Agent, or Firm* — Schwegman Lundberg & Woessner, P.A.

(57) ABSTRACT

Multi-layered prosthetic constructs, kits, and methods are disclosed. A prosthetic construct can include a first ceramic component having a first surface, the first ceramic component comprising a first ceramic material, and a second ceramic component having a second surface disposed on the first surface of the first ceramic component, the second ceramic component comprising a second ceramic material. The second ceramic material of the second ceramic component can exert a compressive force on the first ceramic material. A ceramic material of the second ceramic component can include a different coefficient of thermal expansion than a ceramic material of the first ceramic component. Optionally, a ceramic construct can include a ceramic component and a membrane disposed onto and bonded to at least a portion of the ceramic component, the membrane configured to provide fracture reinforcement to the ceramic component.

13 Claims, 7 Drawing Sheets

(51) Int. Cl.
*A61F 2/30* (2006.01)
*B29C 65/66* (2006.01)

(52) U.S. Cl.
CPC .............. *A61F 2310/00293* (2013.01); *A61F 2310/00317* (2013.01); *A61F 2310/00323* (2013.01); *B29C 65/665* (2013.01)

(56) References Cited

U.S. PATENT DOCUMENTS

| | | | |
|---|---|---|---|
| 4,969,913 A * | 11/1990 | Ojima | 623/66.1 |
| 5,037,438 A | 8/1991 | Davidson | |
| 5,871,547 A | 2/1999 | Abouaf et al. | |
| 7,252,684 B2 | 8/2007 | Dearnaley | |
| 7,332,216 B2 | 2/2008 | Hashimoto et al. | |
| 7,695,521 B2 | 4/2010 | Ely et al. | |
| 2007/0032877 A1 | 2/2007 | Whiteside | |
| 2009/0005878 A1 * | 1/2009 | Tuke et al. | 623/22.24 |
| 2011/0125277 A1 * | 5/2011 | Nygren | A61F 2/30 623/20.14 |
| 2012/0172998 A1 * | 7/2012 | Oishi | 623/23.61 |

OTHER PUBLICATIONS

"JP10328292A, English Translation obtained from LexisNexis® TotalPatent® on Jul. 8, 2015", 11 pgs.

* cited by examiner

MULTI-LAYERED PROSTHETIC CONSTRUCTS, KITS, AND METHODS

CLAIM OF PRIORITY

This application claims the benefit under 35 U.S.C. §119 of U.S. Provisional Patent Application Ser. No. 61/637,024, entitled "MULTI-LAYERED PROSTHETIC CONSTRUCTS, KITS, AND METHODS", and filed on Apr. 23, 2012, which is herein incorporated by reference in its entirety.

BACKGROUND

Prosthetic devices are available to replace bodily components or portions of bodily components that cannot be regenerated or are no longer functioning properly. Examples of prosthetic devices include heart valves, pacemakers, spinal, dental or breast implants, collagen for soft tissue augmentation, and orthopedic devices, such as artificial knee and hip implants.

Existing artificial joints often include a component that articulates against another component, such as a metal or metal alloy ball that articulates within a cup-shaped component made of a high molecular weight polymer placed in a joint socket. Artificial joints can be used to replace hip, knee, shoulder, and other joints in order to restore function after degeneration, accidents, and sport injuries.

SUMMARY

The present inventor recognizes, among other things, that existing artificial joints prematurely fail and need to be replaced. Additionally, due to localized clinical load associated with interacting ball and socket components, small particles can break off from a surface of an existing artificial joint component and contaminate surrounding bodily tissue. The body's immune system attempts to degrade the small particles by secreting enzymes, which can kill the adjacent bone cells or cause osteolysis and lead to mechanical loosening and failure of the artificial joint. The rate of wear of artificial joint components can be dependent upon a number of factors, including the relative hardness and surface finish of materials that constitute the components, the frictional coefficient between the components, the load applied, or the clinical loads generated at the articulating surfaces of the components.

The present disclosure is directed to multi-layered prosthetic constructs, kits, and methods. A multi-layer construct according to the present disclosure can provide a compressive stress from one ceramic component to another ceramic component, for example to offset a clinical load that can be exerted on the prosthetic construct, to increase strength of the prosthetic construct, to increase toughness of the prosthetic construct, to change the failure mode of the prosthetic construct, or to reduce adverse consequences of a failure mode of the prosthetic construct. In an example, one ceramic component induces a compressive stress on another ceramic component that can offset a clinical load on the combined ceramic components and can make fracture of the prosthetic construct less likely. In another example, the first and second ceramic components can be configured so that when the prosthetic construct fails, the failure mode is benign, such as by forming non-sharp pieces that are less likely to result in injury or pain for the patient or by forming pieces that are radio-opaque or radio-translucent so that they can be discoverable by a medical practitioner upon inspection by an imaging device, such as X-ray, MRI, CAT scan, PET scan, or other imaging devices.

In an example, the present disclosure is directed to a prosthetic construct including a first ceramic component having a first surface and a second ceramic component having a second surface disposed on the first surface of the first ceramic component. The first ceramic component comprises a first ceramic material, and the second ceramic component comprises a second ceramic material, wherein the second ceramic material of the second ceramic component exerts a compressive force on the first ceramic material.

In an example, the present disclosure is directed to a method of fabricating a prosthetic construct. The method comprises forming a first ceramic component having a first surface, the first ceramic component comprising a first ceramic material, forming a second ceramic component having a second surface, the second ceramic component comprising a second ceramic material, disposing the second surface of the second ceramic component on the first surface of the first ceramic component, heating the first ceramic material and the second ceramic material, and cooling the first and second ceramic components so that the second ceramic component induces a compressive stress on the first ceramic component.

The present disclosure is also directed to prosthetic constructs, kits, and methods wherein fractured portions of a prosthetic construct are held together so that, upon failure of the prosthetic construct, the fractured portions can remain generally together in the same structure to provide for easier recovery and so that release of one or more of the fractured portions into the patient is less likely in order to reduce the likelihood of further injury or pain for the patient.

In an example, the present disclosure is directed to a prosthetic construct comprising a ceramic component and a membrane disposed between and bonded to portions of the ceramic component, the membrane configured to provide fracture reinforcement to the ceramic component.

In an example, the present disclosure is directed to a method of fabricating a prosthetic construct. The method comprises forming a first component having a first surface, the first component comprising a ceramic material, forming a second component having a second surface, disposing a membrane between the first component and the second component so that the membrane is between the first surface and the second surface, and bonding the membrane to at least a portion of the first component and to at least a portion of the second component, wherein the membrane is configured to provide for fracture reinforcement to one or both of the first component and the second component.

This summary is intended to provide an overview of subject matter of the present disclosure. It is not intended to provide an exclusive or exhaustive explanation of the invention. The detailed description is included to provide further information about the present disclosure.

BRIEF DESCRIPTION OF THE DRAWINGS

In the drawings, like numerals can be used to describe similar elements throughout the several views. Like numerals having different letter suffixes can be used to represent different views of similar elements. The drawings illustrate generally, by way of example, but not by way of limitation, various embodiments discussed in the present document.

DETAILED DESCRIPTION

The present disclosure is directed to multi-layered prosthetic constructs, kits, and methods. A multi-layer construct according to the present disclosure can provide a compressive stress from one ceramic component to another ceramic component, for example to offset a clinical load that can be exerted on the prosthetic construct, to increase strength of the prosthetic construct, to increase toughness of the prosthetic construct, to change the failure mode of the prosthetic construct, and/or to reduce adverse consequences of a failure mode of the prosthetic construct.

Orthopedic implants often comprise articulating joints, such that the wear resistance of materials used to make orthopedic implants can be of interest. For example, an orthopedic hip implant can comprise a femoral head that articulates within the patient's acetabulum or within an artificial acetabular cup placed within the acetabulum. The femoral head can, in certain instances, be made from a metal or metal alloy, such as a titanium alloy or a cobalt-chrome alloy, while the articulating surface of the acetabular cup can be made from a low bearing polymer, such as polyethylene.

In recent years, ceramics have become an area of interest as a material of construction for articulating joints. In particular, ceramics can be of interest for any wear surface because ceramics can be very hard, resistant to wear, and can have a smoother surface than metal components, allowing for reduced wear of polymer bearing components. In addition, ceramic materials can be biocompatible and nontoxic, so that even if some ceramic material does wear from a ceramic component, it will be nontoxic for the patient. Ceramic materials can also provide very low friction when articulating against other components.

In addition, ceramics can be durable and generally do not fracture or chip in normal usage. They can be inert in biological fluids, and can have a stable structure that does not degrade over time or when exposed in a biological environment. Ceramics also can be readily fabricated, can be made economically, can be relatively easy to implant, and can have a long service life.

Although ceramic materials are generally durable, they are not completely resistant to fracture, which can lead to failure of the component. Fracture can occur, for example, when a clinical load is repeatedly applied to the ceramic component. The present disclosure is directed to ceramic components and methods that have increased resistance to fracture or other mechanical failure of the ceramic components. Alternatively, the present disclosure is directed to ceramic components that are configured such that if they fail, they will fail in a more benign way.

In an example, an outer layer ceramic component induces an inwardly-acting compressive stress on an inner ceramic component that can offset a clinical load on the combined ceramic components and can make fracture of the prosthetic construct less likely. In an example, the first and second ceramic components can be configured so that if the prosthetic construct fails, the failure mode is benign, such as by forming non-sharp pieces and/or pieces that are radio-opaque or radio-translucent so that they can be discoverable by a medical practitioner upon inspection with an imaging device, such as X-ray, MRI, a CAT scan, a PET scan, or other imaging devices. A total joint implant that can be made very strong and hard with a very smooth surface that is resistant to abrasion and corrosion would be a major improvement over currently available devices. Such a device would produce less wear when articulating against polymeric components and would have the potential of lasting the lifetime of a young and active patient.

Figure 1:
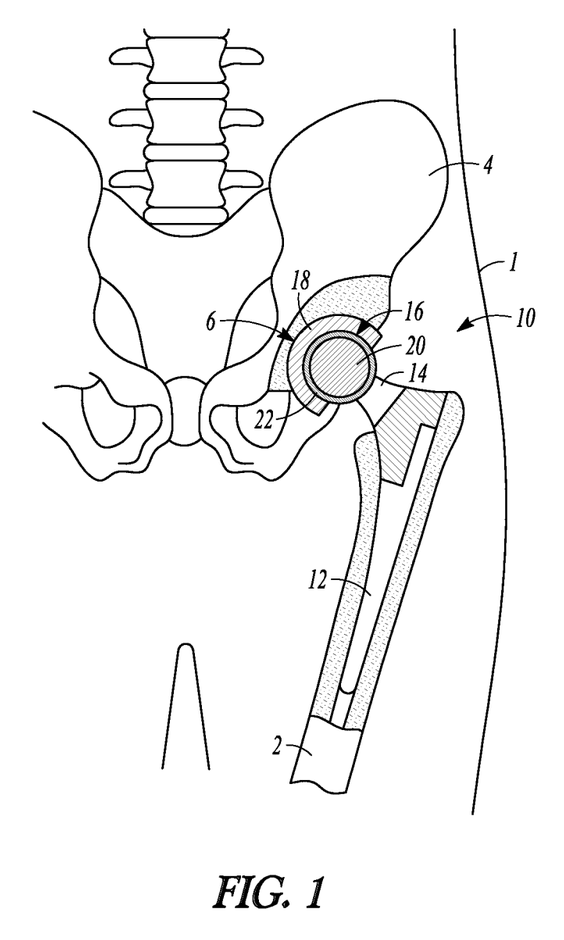
FIG. 1 is a schematic diagram of an example orthopedic hip implant having a ceramic femoral head comprising a first ceramic component and a second ceramic component disposed on the first ceramic component.

FIG. 1 is a schematic diagram of an exemplary orthopedic hip implant 10 implanted within a patient 1. The hip implant 10 can comprise a stem 12, a neck 14, and a head 16. The stem 12 can be implanted within the femur 2 of patient 1, such as by being inserted and affixed (e.g., naturally or in conjunction with an adhesive, such as bone cement) into the medullary canal of the femur 2. The neck 14 can be integrally formed with or coupled to the stem 12, and the head 16 can be coupled to or otherwise associated with the neck 14. The head 16 can engage the acetabulum 6 of the patient's pelvis 4. The acetabulum can be prepared to receive an acetabular cup 18, such as the Allofit®, Trilogy® or Continuum® cup available from Zimmer, Inc. (Warsaw, Ind.), wherein the head 16 can smoothly slide while articulating within acetabulum 6.

The head 16 can comprise a ceramic material. As described above, a ceramic material can provide for high hardness of the head 16, low friction between the head 16 and the acetabulum 6 or the acetabular cup 18, and good wear resistance. A ceramic head 16 can also provide for biocompatibility and nontoxcity of the head 16 within the patient 1. In an example, shown in FIGS. 1 and 2, the head 16 comprises a first ceramic component 20 and a second ceramic component 22, wherein the second ceramic component 22 is disposed on the first ceramic component 20. In the example of a ceramic head 16 of a hip implant 10, shown in FIG. 1, the first ceramic component 20 can be referred to as a core 20 and the second ceramic component 22 can be referred to as a shell 22.

Figure 2:
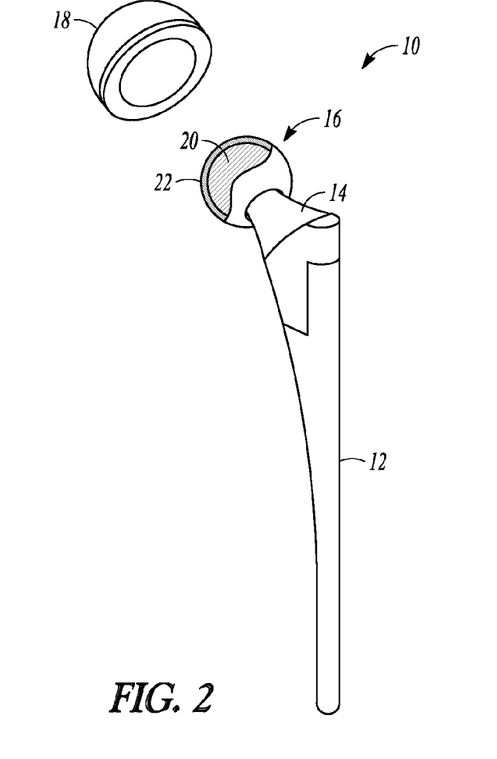
FIG. 2 is a perspective view of an example orthopedic hip implant having a ceramic femoral head comprising a first ceramic component and a second ceramic component disposed on the first ceramic component.

The first ceramic component 20 can comprise a first ceramic material, and the second ceramic component 22 can comprise a second ceramic material, wherein the second ceramic material of the second ceramic component 22 can have at least one material property that is different from that of the first ceramic material of the first ceramic component 20. The second ceramic material of the second ceramic component 22 can exert a compressive force on the first ceramic material of the first ceramic component 20. The compressive force of the second ceramic component 22 can increase the strength or toughness of the head 16 or changes the failure mode of the head 16 relative to the individual strength, toughness, or failure mode of the first ceramic component 20 or the second ceramic component 22.

Figure 3:
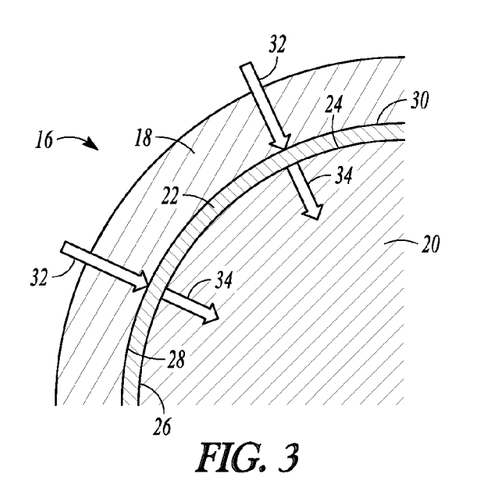
FIG. 3 is a cross-sectional view of an example ceramic femoral head for use with an orthopedic hip implant.

FIG. 3 shows a cross-section of the head 16 that can be used, for example, in the exemplary hip implant 10 of FIGS. 1 and 2. As shown in FIG. 3, the second ceramic component 22 can be disposed on the first ceramic component 20, for example as an outer ceramic shell 22 disposed over an inner ceramic layer or core 20. The first ceramic component 20 can comprise a first surface 24, such as an outer surface 24, and the second ceramic component 22 can comprise a second surface 26, such as an inner surface 26, wherein the second surface 26 of the second ceramic component 22 can be disposed on the first surface 24 of the first ceramic component 20.

The first ceramic component 20 and the second ceramic component 22 can be configured so that the compressive force exerted by the second ceramic component 22 onto the first ceramic component 20 can be exerted in generally the same direction as an expected stress on the head 16, as referred to herein as the "clinical load." In the case of head 16 shown in FIGS. 1-3, the clinical load acting on the head 16 can be expected to be exerted generally radially inwardly from the contact between the head 16 and the acetabulum 6 or the acetabular cup 18. The physical structure and the material or materials used to make up the first ceramic component 20, the second ceramic component 22, or both, can be modified to provide for a direction of compression by the second ceramic component 22 that is substantially in the same direction as the expected clinical load on the head 16.

As shown in FIG. 3, the expected force to be exerted on the head 16 can be exerted by the acetabular cup 18 onto the head 16, for example by an inner surface 28 of the acetabular cup 18 acting against an outer surface 30 of the head 16. The force being exerted by the acetabular cup 18 is shown conceptually by arrows 32 in FIG. 3. The first ceramic component 20 and the second ceramic component 22 can be configured so that a compressive force can be exerted by the second ceramic component 22 that is substantially in the same direction as, e.g., that is substantially parallel to, the clinical load 32 being exerted on the head 16 by the acetabular cup 18. The compressive force being exerted by the second ceramic component 22 on the first ceramic component 20 is shown conceptually by arrows 34 in FIG. 3.

Figure 4:
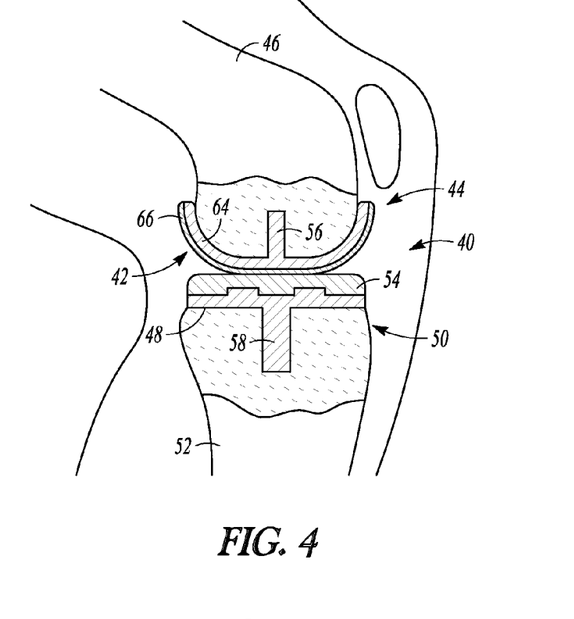
FIG. 4 is a schematic diagram of an example orthopedic knee implant implanted within a patient.

The use of a multi-layer ceramic construct can be used in orthopedic components other than hip implants. FIG. 4 shows an artificial knee implant 40 that can comprise a multi-layer ceramic construct in at least one of the components of the knee implant 40. The knee implant 40 can comprise a femoral component 42 coupled to a distal end 44 of the patient's femur 46, a tibial component 48 coupled to a proximal end 50 of the patient's tibia 52, and a bearing component 54 positioned between the femoral component 42 and the tibial component 48. The bearing component 54 can be coupled to the tibial component 48 while the femoral component 42 can articulate against the bearing component 54 to provide for the articulating motion of the knee implant 40. The femoral component 42 can be coupled to the femur 46 with one or more posts 56 that are implanted within the femur 46 by inserting the posts 56 into the femur 46 and affixing (e.g., naturally or in conjunction with an adhesive, such as bone cement) the femoral component 42 to the femur 46. Similarly, the tibial component 48 can be coupled to the tibia 52 with one or more posts 58 that are inserted and affixed (e.g., either naturally or in conjunction with an adhesive, such as bone cement) to the tibia 52, such as in the medullary canal of the tibia 52.

Figure 5:
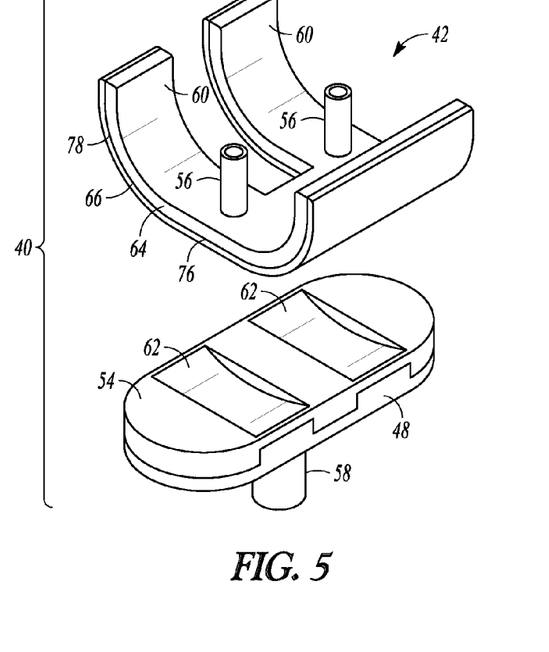
FIG. 5 is an exploded perspective view of an example orthopedic knee implant.

FIG. 5 shows an exploded perspective view of the exemplary knee implant 40. As is best seen in FIG. 5, the femoral component 42 can comprise a pair of condyl portions 60 that engage with a pair of slots 62 in the bearing component 54 to help ensure aligned articulation between the femoral component 42 and the bearing component 54.

As shown in FIG. 5, at least one of the components of the knee implant 40 can comprise a multi-layer ceramic construct comprising at least a first ceramic component and a second ceramic component disposed on the first ceramic component. The femoral component 42 can comprise a first ceramic component 64 and a second ceramic component 66. The first ceramic component 64 can comprise an inner ceramic component 64 and the second ceramic component 66 can comprise an outer ceramic component 66 disposed on the inner ceramic component 64.

Figure 6A:
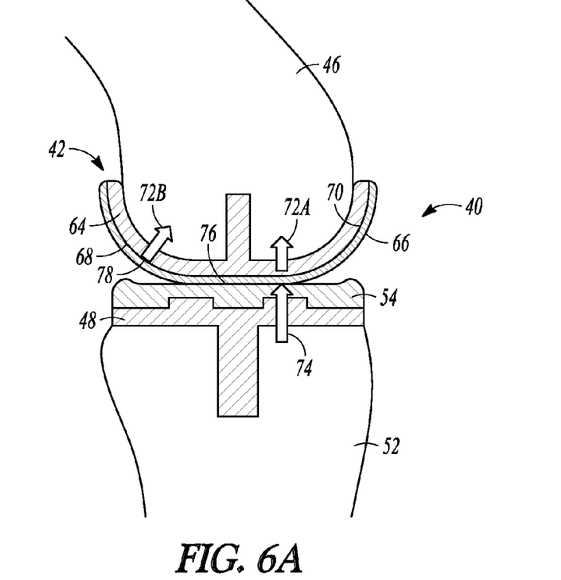
FIGS. 6A and 6B are cross-sectional views of an example orthopedic knee implant in an extended mode and a bent mode, respectively.
Figure 6B:
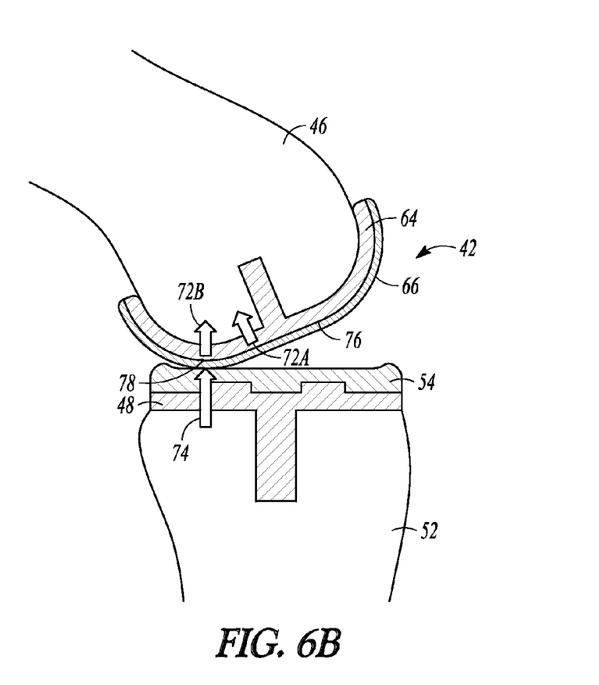

FIGS. 6A and 6B show cross-sectional views of the knee implant 40. The second ceramic component 66 of the femoral component 42 can be disposed on the first ceramic component 64, for example as an outer layer disposed over an inner layer. The first ceramic component 64 can comprise a first surface 68, such as an outer surface 68 of the inner layer 64, and the second ceramic component 66 can comprise a second surface 70, such as an inner surface 70 of outer layer 66, wherein the second surface 70 of the second ceramic component 66 can be disposed on the first surface 68 of the first ceramic component 64.

As described above with respect to the exemplary hip implant 10, the first ceramic component 64 and the second ceramic component 66 can be configured so that the one of the components exerts a compressive force on the other component, such as the second ceramic component 66 exerting a compressive force on the first ceramic component 64. The compressive force exerted by the second ceramic component 66 onto the first ceramic component 64 is shown conceptually in FIGS. 6A and 6B by arrows 72A and 72B, collectively referred to herein as "compressive force 72." The ceramic components 64, 66 can be configured so that the compressive force 72 is in substantially the same direction as, e.g., substantially parallel to, the expected force to be exerted onto the femoral component 42, also referred to as the clinical load. For the knee implant 40, a clinical load can be expected to be exerted from the bearing component 54 and the tibial component 48 onto the femoral component 40. This expected clinical load can be exerted generally upwardly from the tibia 52 toward the femur 46. The expected clinical load is shown conceptually in FIGS. 6A and 6B as arrow 74.

The compressive force exerted by the second component 66 onto the first ceramic component 64 can be non-uniform in direction. For example, as shown in FIG. 6A, when the patient's knee is straight, e.g., when the femur 46 and the tibia 52 are generally axially aligned with each other, the clinical load 74 exerted onto the femoral component 42 can be generally perpendicular to a middle portion 76 of the femoral component 42. Therefore, the compressive force exerted by the second component 66 on the first component 64 at the middle portion 76, represented by force arrow 72A, also can be generally perpendicular to the middle portion 76 so that the compressive force 72A is oriented in substantially the same direction as the expected clinical load 74 that is exerted onto the femoral component 42 at the middle portion 76, which is the portion of the femoral component that is engaged when the patient's knee is straight.

Similarly, when the patient bends the knee, e.g., so that the femur 46 and the tibia 52 are angled with respect to each other, as shown in FIG. 6B, then the location and orientation of the clinical load 74 can change as the femoral component 42 articulates against the bearing component 54. In the example shown in FIG. 6B, the clinical load 74 can be exerted onto a rear generally curved portion 78, e.g., on the condyl portions 60. In such a situation, the clinical load 74 can act in a direction that is angled with respect to the compressive force 72A at the middle portion 76 of the femoral component 42. Therefore, the first ceramic component 64 and the second ceramic component 66 can be configured so that at the rear curved portion 78, the compressive force exerted by the second ceramic component 66 onto the first ceramic component 64 can be exerted generally inwardly from the curve (e.g., generally normal to a tangent of the curve that forms the rear curved portion 78) so that when the knee is bent, the compressive force 72B at the rear portion 78 will be in generally the same direction, e.g., generally parallel to, the expected clinical load 74.

The compressive force between a first ceramic component and a second ceramic component, for example between the second ceramic component 22 and the first ceramic component 20 of the head 16 of the hip implant 10 or between the second ceramic component 66 and the first ceramic component 64 of the femoral component 42 of the knee implant 40, can occur due to differences in physical characteristics between the first ceramic component 20, 64 and the second ceramic component 22, 66, such as differences in coefficients of thermal expansion, differences in density, or because of differences in physical dimensions, such as thickness or relative thickness.

The compressive force can occur due to a difference between the material or materials used to form the first ceramic component 20, 64 and the second ceramic component 22, 66, wherein a first ceramic material can be used to form the first ceramic component 20, 64 and a second ceramic material can be used to form the second ceramic component 22, 66. As described in more detail below, a ceramic material can be made from one or more ceramic powders or particles and one or more binders that bind the ceramic powder or particles in a "green state." The green state material can be subjected to high temperatures in order to drive out the binder and to sinter the ceramic powder or particles together.

Suitable ceramic compounds that can be used to make either the first ceramic material or the second ceramic material include, but are not limited to, at least one of alumina (also known as aluminum oxide, $Al_2O_3$), zirconia (also known as zirconium dioxide, $ZrO_2$), silica (also known as silicon dioxide, $SiO_2$), hydroxyapatite ($Ca_{10}(PO_4)_6(OH)_2$), titanium nitride (TiN), and silicon nitride ($Si_3N_4$).

The difference between the first ceramic material and the second ceramic material can comprise the specific ceramic compound or compounds used to form each ceramic component, e.g., the compound or compounds of the ceramic particles that are bound together and sintered to form the ceramic material. For example, the first ceramic material can be made from a first ceramic compound or combination of compounds, while the second ceramic material can be made from a second ceramic compound or combination of compounds.

The first ceramic material of the first ceramic component 20, 64 can comprise a first ceramic compound, e.g., alumina, and the second ceramic material of the second ceramic component 22, 66 can comprise a second ceramic compound that is different from the first ceramic compound, e.g., zirconia, so that the difference in material can lead to a differential in the coefficient of thermal expansion, leading to a compressive force being exerted by the second ceramic component 22, 66 onto the first ceramic component 20, 64. The coefficient of thermal expansion can be higher in an outer component, such as the second ceramic component 22 shown in FIGS. 1-3 or the second ceramic component 66 shown in FIGS. 5, 6A, and 6B, than in an inner component, such as the first ceramic component 20 shown in FIGS. 1-3 or the first ceramic component 64 shown in FIGS. 5, 6A, and 6B.

The first ceramic material of the first ceramic component 20, 64 can comprise a ceramic compound, e.g., alumina, and the second ceramic material of the second ceramic component 22, 66 can comprise the same ceramic compound, e.g., also alumina, but the properties of the ceramic compound for the second ceramic material can be different from that of the first ceramic material, such as different particle size of the particles used to form the ceramic material, a different binder or combination of binders used to form the green state, a different percentage of the ceramic compound used to form the green state (e.g., a different weight ratio of binder to ceramic particles), or the use of different additives. The first ceramic material of the first ceramic component 20, 64 can comprise a first mixture of ceramic compounds, e.g., alumina and zirconia in a first weight ratio, and the second ceramic material of the second ceramic component 22, 66 can comprise a second mixture of ceramic compounds, e.g., different ceramic compounds (such as silica and titanium nitride, or alumina and silicon nitride) or the same ceramic compounds but in a second weight ratio.

The first ceramic material or the second ceramic material can be configured so that if the first ceramic component 20, 64 or the second ceramic component 22, 66 fails so that a portion of one of the ceramic components breaks off, also referred to herein as a shard, that the shard will be in a benign form within the patient. In previous ceramic components, shards that broke off from a ceramic component were often sharp. The first ceramic material or the second ceramic material, or both, can be formed so that, if a ceramic component fails and shards form, the shards are not sharp, such as by engineering fault lines into the ceramic material that, when broken, result in shards having rounded edges or edges with another benign profile.

The ceramic material of the first ceramic component 20, 64 or the second ceramic component 22, 66, or both, can be configured so that it will be radiotranslucent or radioopaque when viewed by an imaging device, such as an X-ray machine, a magnetic resonance imaging (MRI) device, a computed tomography (CT) scan, a computed axial tomography (CAT) scan, a positron emission tomography (PET) scan, or an ultrasound device. In previous ceramic components, shards that broke off from a ceramic component were often difficult or impossible to find via inspection by an imaging device. The ceramic material of the first ceramic component 20, 64 or the second ceramic component 22, 66, or both, can be configured so that if shards break off from one or both of the ceramic components, the shards will be visible by the imaging device. The shards can be made visible by an imaging device by incorporating additives into one or both of the ceramic components that can impart radiopacity, such as, but not limited to, metal oxides, metal phosphates, and metal sulfates, such as barium sulfate, barium titanate, zirconium oxide, ytterbium fluoride, barium phosphate, and ytterbium oxide.

Prosthetic constructs in accordance with the present disclosure are not limited to artificial hip implants or knee joints such as the artificial hip implant 10 of FIGS. 1-3 or the artificial knee implant 40 of FIGS. 4-6. Rather, multi-layered ceramic constructs similar to those described above with respect to FIGS. 1-6 can be implemented in other orthopedic devices including, but not limited to, a prosthetic shoulder implant, a prosthetic arm implant, a prosthetic elbow implant, a prosthetic finger implant, a prosthetic spine implant, a prosthetic toe implant, a prosthetic ankle implant, and a prosthetic trauma implant.

Figure 7:
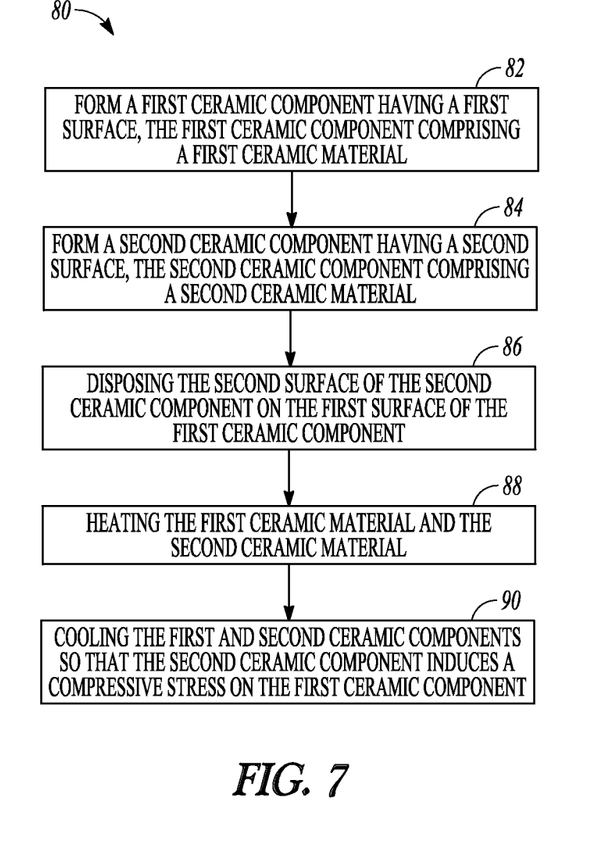
FIG. 7 is a flow diagram of an example method of manufacturing a component of an orthopedic implant, the component comprising a first ceramic component and a second ceramic component disposed on the first ceramic component.

Turning now to methods for manufacturing a prosthetic construct as described herein, FIG. 7 shows a flow chart of an exemplary method 80 for manufacturing a multi-layered ceramic component. The method 80 can comprise, at 82, forming a first ceramic component 20, 64 having a first surface 24, 68. The first ceramic component 20, 64 can comprise a first ceramic material. At 84, a second ceramic component 22, 66 having a second surface 26, 70 can be formed. The second ceramic component 22, 66 can comprise a second ceramic material.

At 86, the second surface 26, 70 of the second ceramic component 22, 66 can be disposed on the first surface 24, 68 of the first ceramic component 20, 64. At 88, at least the second ceramic component 22, 66 can be heated in order to cause the second ceramic component 22, 66 to expand due to thermal expansion. As shown in FIG. 7, in an example, both the first ceramic component 20, 64 and the second ceramic component 22, 66 can be heated.

After, the method comprises, at 90, the first ceramic component 20, 64 and the second ceramic component 22, 66 can be cooled, after heating at least the second ceramic component 22, 66, or heating both the first ceramic component 20, 64 and the second ceramic component 22, 66. The cooling can be such that the second ceramic component 22, 66 induces a compressive stress onto the first ceramic component 20, 64. The compressive stress exerted by the second ceramic component 22, 66 onto the first ceramic component 20, 64 can result from the second ceramic component 22, 66 contracting at a faster rate than the first ceramic component 20, 64 due to a higher coefficient of thermal expansion for the second ceramic component 22, 66 versus the coefficient of thermal expansion for the first ceramic component 20, 64.

Forming each of the first ceramic component 20, 64 and the second ceramic component 22, 66 can be accomplished using any method of forming ceramic bodies as generally known in the art. For example, the first ceramic component 20, 64 can be formed by binding together particles of the first ceramic material with a binder in the desired shape of the first ceramic component 20, 64. The bound first ceramic particles can then be heated to a sintering temperature that can be capable of driving off the binder and of sintering the particles of the first ceramic material together. Similarly, the second ceramic component 22, 66 can be formed by binding together particles of the second ceramic material with a binder in the desired shape of the second ceramic component 22, 66. The bound second ceramic particles can then be heated to a sintering temperature that can be capable of driving off the binder and of sintering the particles of the second ceramic material together.

Forming the first ceramic component 20, 64 and forming the second ceramic component 22, 66, at 82 and 84, respectively, can be done in any order. For example, the first ceramic component 20, 64 can be formed before the second ceramic component 22, 66 is formed, or the ceramic components can be formed in the opposite order. Alternatively, the first ceramic component 20, 64 can be formed first, e.g., by binding particles of a first ceramic material and then sintering the bound particles. After forming and sintering the first ceramic component 20, 64, particles of a second ceramic material can be applied to the first ceramic component 20, 64, e.g., by applying a mixture of the particles of the second ceramic material and a binder on top of the first surface 24, 68 of the first ceramic component 20, 64 and shaping the mixture into a desired shape of the second ceramic component 22, 66. The shaped mixture of the particles of the second ceramic material and the binder can then be heated to a sintering temperature to sinter the particles of the second ceramic material in order to form the second ceramic component 22, 66 on the first ceramic component 20, 64.

In another embodiment, the particles of the first ceramic material can be bound with a binder and then sintered, while the particles of the second ceramic material can be bound with a binder and sintered separate from the binding and sintering of the particles of the first ceramic material, and then the two sintered components, e.g., the first ceramic component 20, 64 and the second ceramic component 22, 66, can be combined so that the second surface 26, 70 of the second ceramic component 22, 66 is disposed on the first surface 24, 68 of the first ceramic component 20, 64.

In yet another embodiment, particles of the first ceramic material can be combined with a binder and shaped into a desired shape for the first ceramic component 20, 64, where the body can be in a green state, e.g., the unsintered state. Then, a mixture of particles of the second ceramic material and a binder can be applied to the green-state body of the first ceramic material and the binder and shaped into a desired shape for the second ceramic component 22, 66 so that a green-state body of particles of the second ceramic material can be disposed on a green-state body of particles of the first ceramic material. The two green-state bodies can then be heated to sinter the ceramic materials of both bodies and to drive off the binders from the bodies. In this embodiment, heating the first ceramic material and the second ceramic material, at 88, can provide for thermal expansion of the ceramic materials, and can also provide for sintering of the ceramic materials and driving off of binder.

Cooling the first ceramic component 20, 64 and the second ceramic component 22, 66, at 90, can comprise actively cooling the ceramic components, such as with a cooling apparatus, for example a cooler, a heat exchanger, or a refrigerator, or it can comprise letting the first ceramic component 20, 64 and the second ceramic component 22, 66 passively cool to ambient temperature.

Figure 8:
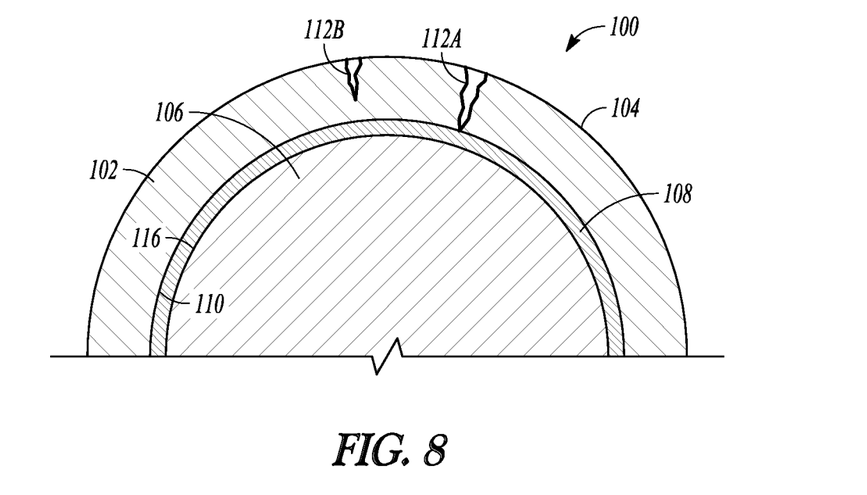
FIG. 8 is a cross-sectional view of an example ceramic component for use with an orthopedic implant, the ceramic component comprising a membrane for reducing or preventing migration of cracks within the ceramic component.

The present disclosure also describes prosthetic constructs, kits, and methods wherein fractured portions of a prosthetic construct are held together so that, upon failure of the prosthetic construct, the fractured portions can remain generally together in the same structure to provide for easier recovery and so that release of one or more of the fractured portions into the patient is less likely in order to reduce the likelihood of further injury or pain for the patient. FIG. 8 shows a conceptual cross-sectional view of a component 100 of a prosthetic implant, such as a head of a hip implant, or a femoral component or a tibial component of a knee implant. As shown, component 100 can comprise at least one ceramic component 102 having an outer surface 104. The ceramic component 102 can comprise a ceramic outer covering of the head that articulates within the acetabulum, for example within an acetabular cup, similar to the head 16 and acetabular cup 18 described above with respect to hip implant 10 of FIG. 1. The outer surface 104 can articulate within an acetabular cup.

As shown in FIG. 8, the component 102 can have a second component 106, such as an inner component 106, which also can be formed from a ceramic material. The second component 106 can also comprise a ceramic material, which can be the same as or different from the ceramic material of the first or outer component 102. Suitable ceramic materials that can be used to make the first component 102 or the second component 104 include, but are not limited to, at least one of alumina ($Al_2O_3$), zirconia ($ZrO_2$), silica ($SiO_2$), hydroxyapatite ($Ca_{10}(PO_4)_6(OH)_2$), titanium nitride (TiN), and silicon nitride ($Si_3N_4$). The second component 106 does not have to be made from a ceramic material, however, and can be made from other materials, including, but not limited to, metals, such as titanium, titanium alloys, and cobalt-chrome, plastics, such as polyethylene or polyether ether ketone (also known as PEEK), or other polymeric materials, such as rubber, or silicone rubber.

As shown in FIG. 8, the component 100 can further comprise a membrane 108 that can be disposed on a surface of a ceramic component, such as an inner surface 110 of the ceramic component 102. The membrane 108 can be bonded to at least a portion of the ceramic component 102, such as being bonded to at least a portion of the inner surface 110. The membrane 108 can be disposed between the outer ceramic component 102 and the inner component 104, which can be a ceramic component 104. The membrane 108 can be bonded to at least a portion of each of the first ceramic component 102 and the second ceramic component 104. Alternatively, the component 100 can comprise a single ceramic component, similar to outer ceramic component 102, with a membrane, similar to membrane 108, disposed on its inner surface.

The membrane 108 can be configured to provide for reinforcement of the outer ceramic component 102, or to the inner component 104, or both. For example, the membrane 108 can be configured to prevent or reduce the likelihood of the outer ceramic component 102 from fracturing or failing or to provide for prevention or a reduced likelihood of the migration of fractures in the outer ceramic component 102. As shown in FIG. 8, one or more cracks 112A and 112B can form in the ceramic component 102, such as from articulation of the component 100 against another component, such as a head of a hip implant against an acetabulum or an acetabular cup or as a femoral component against a tibial component of a knee implant. As shown in FIG. 8, a first crack 112A has formed to the point that the crack 112A has encountered the membrane 108. The membrane 108 can be configured to resist tearing when this occurs and to prevent or reduce further separation of pieces of the ceramic component 102 or enlarging of the crack 112A. The membrane 108 can also be configured so that it reinforces the ceramic component 102 so that a crack that has not reached the membrane 108, such as a second crack 112B, can be reinforced to prevent further downward or inward migration by the crack 112B. In other words, in addition to stopping or slowing the first crack 112A at the membrane 108 itself, the membrane 108 can also provide for reinforcement that prevents or reduces migration of a crack 112B within the ceramic material before the crack 112B reaches the membrane 108, further reinforcing the ceramic component 102.

Figure 9:
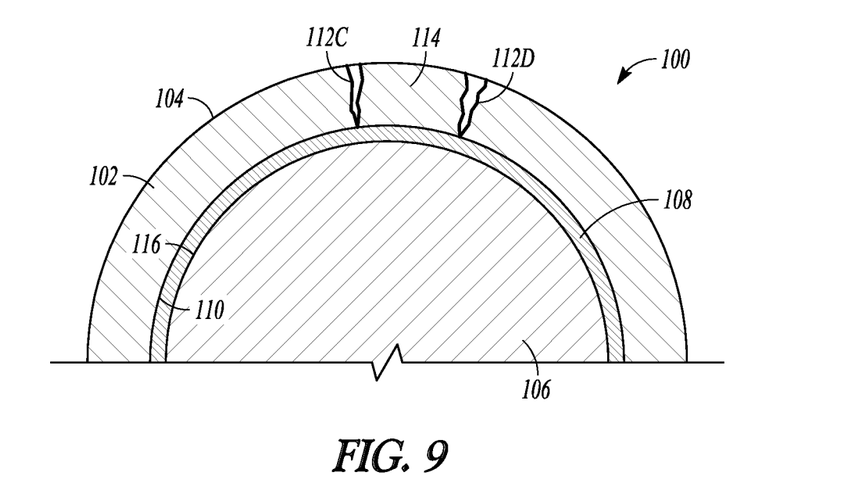
FIG. 9 is a cross-sectional view of the example ceramic component of FIG. 7 after a plurality of cracks have formed a shard of the ceramic material of the component.

The membrane 108 can be configured to retain a portion of the ceramic component 102, also referred to herein as a shard of ceramic, which could otherwise have broken off from the ceramic component 102. Illustratively, FIG. 9 shows an example where both a first crack 112C and a second crack 112D have formed in the ceramic component 102 and have reached the membrane 108. The cracks 112C, 112D can also combine with each other or with other cracks (not shown) so that a shard 114 becomes separated from the rest of the ceramic component 102. The membrane 108 can be configured so that at least a portion of the shard 114 is retained by the membrane 108 to substantially prevent shard 114 from becoming physically separated from the rest of the component 100.

Because it can be difficult to predict where cracks or a shard will form within the ceramic component 102, the membrane 108 can be configured to bind to all of or a substantial portion of the inner surface 110 of the ceramic component 102 so that if a shard, such as shard 114, forms from one or more cracks, the shard will be bound to and retained by the membrane 108. The membrane 108 can be configured to bind to all or substantially the entirety of the inner surface 110.

As shown in FIGS. 8 and 9, the membrane 108 can be disposed between a first ceramic component, such as an outer ceramic component 102, and a second component, such as an inner component 104, which can be made from a ceramic or from another material. The membrane 108 can be bonded to at least a portion of both the first ceramic component 102 and the second component 104, such as at least a portion of an inner surface 110 of the first ceramic component 102 and at least a portion of an outer surface 116 of the second component 104.

The membrane 108 can be made from any material that can bind to the material of the first ceramic component 102 and, if desired, to the material of the second component 104. The material of the membrane 108 can be selected to resist tearing, e.g., when a crack, such as crack 112A, 112B, 112C, or 112D encounters the membrane 108. The material of the membrane 108 also can have a high-fracture toughness and high shear toughness. Suitable materials for use as the membrane 108 include, but are not limited to a biocompatible polymer. The membrane 108 can also comprise an additive, such as a radio-opaque or radio-translucent compound. The radio-opaque or radio-translucent compound can allow at least a portion of the membrane 108 to be detectable by an imaging device, such as an X-ray device, an MRI device, a CAT scan device, or a PET scan device.

Figure 10:
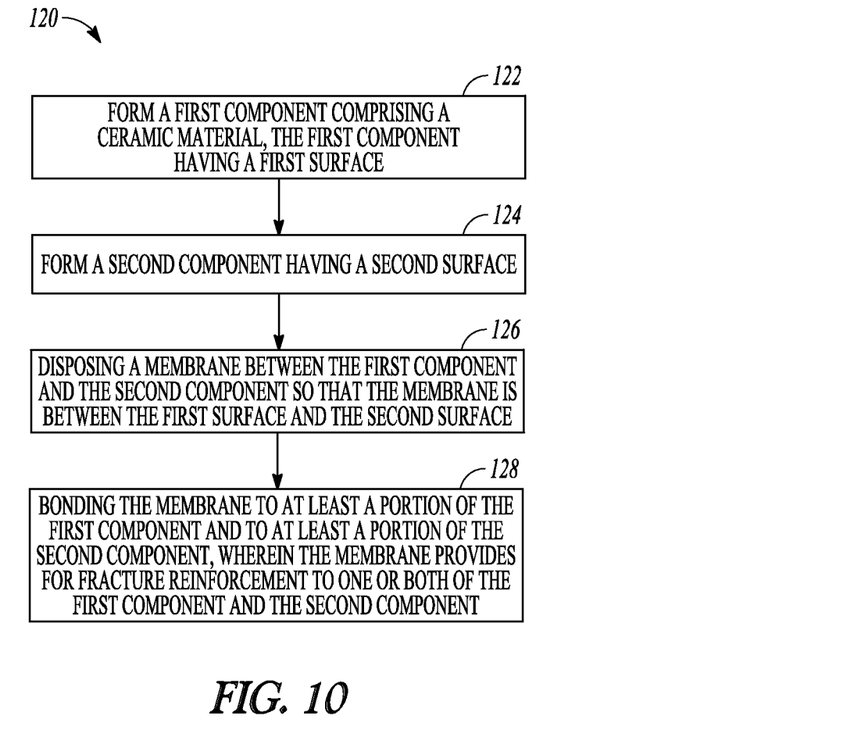
FIG. 10 is a flow diagram of an example method of manufacturing a component of an orthopedic implant, the component comprising a ceramic portion and a membrane for reducing or preventing migration of cracks within the ceramic portion.

FIG. 10 is a flow chart of an exemplary method 120 of manufacturing a prosthetic construct comprising a membrane, such as the component 100 comprising the membrane 108 described above. At 122, a first component comprising a ceramic material can be formed, such as the first ceramic component 102 shown in FIGS. 8 and 9. The first component 102 can have a first surface 110. At 124, a second component can be formed, such as second component 104 shown in FIGS. 8 and 9. The second component 104 can have a second surface 116. At 126, a membrane can be disposed between the first component 102 and the second component 104, such as the membrane 108 shown in FIGS. 8 and 9. After disposing, the membrane 108 can be positioned between the first surface 110 and the second surface 116. At 128, the membrane 108 can be bonded to at least a portion of the first component 102 and to at least a portion of the second component 104. When the membrane 108 is bonded to the portions of the first component 102 and the second component 104, the membrane 108 can provide for fracture reinforcement to one or both of the first component 102 and the second component 104.

In one embodiment, an inner component, for example the second component 104 shown in FIGS. 8 and 9, can be formed first, such as by binding particles of a ceramic material together with a binder and heating the bound particles to sinter the particles together and to drive off the binder, then the membrane 108 can be disposed on the second component 104. The membrane 108 can be bonded to a portion of the second component 104, such as on a portion of the outer surface 116 of the second component 104, or the membrane 108 can be disposed on the second component 104 to be bonded later. The membrane 108 can also be bonded to a portion of the first component 102, such as a portion of the inner surface 110 of the first component 102, or the membrane 108 can be disposed on the first component 102 to be bonded later.

The first component 102 can be formed separately, such as by binding particles of a ceramic material together with a binder and heating the bound particles to sinter the particles together and drive off the binder. After the first component 102 has been formed, the membrane 108 can be positioned between the first component 102 and the second component 104, such as by disposing the first component 102 over the membrane 108 that has been previously disposed on the second component 104, or by disposing the membrane 108 onto the first component 102, such as on the inner surface 110, and then disposing the combination of the first component 102 and the membrane 108 over the second component 104. The membrane 108 can be positioned between the first surface 110 of the first component 102 and the second surface 116 of the second component 104. The membrane 108 can be bonded to a portion of the first component, such as to a portion of the surface 110 of the first component, or the first component 102 can simply be disposed onto the membrane 108. If the membrane 108 is not bonded to the first component 102 or the second component 104 upon positioning the membrane 108 between the components 102, 104, then the method 120 can include bonding the membrane 108 to at least a portion of the first component 102 and to at least a portion of the second component 104, such as by heating the membrane 108 to form a thermal bond between the membrane 108 and the portion of the first component 102 and between the membrane and the portion of the second component 104.

The second component 104 can be formed, such as by binding and then sintering particles of ceramic material, and the membrane 108 can be disposed on the second component 104, and then the first component 102 can be formed over the membrane 108 by applying a mixture of ceramic particles and a binder over the membrane 108 and shaping the mixture into a desired shape of the first component 102. Then, after applying the mixture, the first component 102 can be heated to sinter the particles of ceramic material together and to drive off the binder.

In another embodiment, particles of ceramic material can be combined with a binder and shaped into a desired shape for the second component 104, where the body can be in a green state, e.g., an unsintered state, and then a material of the membrane 108 can be applied to the green-state body of the second component 104. Then, a mixture of particles of ceramic material and a binder can be applied to the green-state body of the second component 104 and the membrane 108 and the mixture of the ceramic particles and binder can be shaped into a desired shape for the first component 102 so that a green-state body of ceramic particles can be disposed on a membrane material, which in turn can be disposed on another green-state body of ceramic particles.

The membrane 108 can be disposed on the inner surface 110 of the green-state first component 102 and the second component 104 can be formed inside the green-state first component 102 and the membrane 108, such as by forming a mixture of particles of ceramic material and a binder and applying the mixture inside the combination of the green-state first component 102 and the membrane 108. Thus, a green-state body of the second component 104 can be formed inside the combination of the green-state first component 102 and the membrane 108.

The two green-state bodies and the membrane material can then be heated to sinter the ceramic materials of both bodies, to drive off the binders from the bodies, and to cause the membrane material to bond to at least a portion of each of the first component 102 and the second component 104. The heating and subsequent cooling of the two ceramic components 102, 104 can also allow for a compressive force to be exerted on the inner component 104 by the outer component 102, similar to the compressive force described above with respect to FIGS. 1-7.

To better illustrate the multi-layered prosthetic constructs, kits, and methods disclosed herein, a non-limiting list of examples is provided here:

Example 1 can include subject matter (such as an apparatus, a device, a method, or one or more means for performing acts), such as can include or use a prosthetic construct comprising a first ceramic component having a first surface, the first ceramic component comprising a first ceramic material. A second ceramic component can be included having a second surface that can be disposed on the first surface of the first ceramic component. The second ceramic component can comprise a second ceramic material, wherein the second ceramic material of the second ceramic component exerts a compressive force on the first ceramic material.

Example 2 can include, or can optionally be combined with the subject matter of Example 1, to optionally include the first and second ceramic components, when combined, increasing a strength or toughness of the prosthetic construct or change a failure mode of the prosthetic construct, relative to individual strengths, toughnesses, or failure modes of the first or second ceramic component, when separate.

Example 3 can include, or can optionally be combined with the subject matter of one or any combination of Examples 1 and 2, to optionally include or use the compressive force being exerted in generally the same direction as an expected clinical load to be exerted on the prosthetic construct.

Example 4 can include, or can optionally be combined with the subject matter of one or any combination of Examples 1-3, to optionally include or use the second ceramic material comprising a different ceramic material than the first ceramic material.

Example 5 can include, or can optionally be combined with the subject matter of one or any combination of Examples 1-4, to optionally include or use the first ceramic material having a value of a material property that is different from a corresponding value of the material property of the second ceramic component. The difference in values of the material property between the first ceramic component and the second ceramic component can contribute to forming the compressive force exerted by the second ceramic component onto the first ceramic component.

Example 6 can include, or can optionally be combined with the subject matter of one or any combination of Examples 1-5, to optionally include or use the second ceramic material of the second ceramic component including a higher coefficient of thermal expansion than the first ceramic material of the first ceramic component.

Example 7 can include, or can optionally be combined with the subject matter of one or any combination of Examples 1-6, to optionally include or use the second surface of the second ceramic component comprising an inner surface and the first surface of the first ceramic component comprises an outer surface, wherein the inner surface can be sized and shaped to receive the outer surface.

Example 8 can include, or can optionally be combined with the subject matter of one or any combination of Examples 1-7, to optionally include or use each of the first and second ceramic components including a generally spherical shape. An outer surface diameter of the generally spherical shape of the first ceramic component can be less than an outer surface diameter of the generally spherical shape of the second ceramic component.

Example 9 can include, or can optionally be combined with the subject matter of one or any combination of Examples 1-8, to optionally include or use the compressive stress being configured to counteract use-based load tensile clinical load.

Example 10 can include, or can optionally be combined with the subject matter of one or any combination of Examples 1-9, to optionally include or use the second ceramic component being sized and shaped to substantially surround the first ceramic component.

Example 11 can include, or can optionally be combined with the subject matter of one or any combination of Examples 1-10, to optionally include or use an outer surface of the second ceramic component including a convex portion defining an articulating bearing surface sized and shaped for seated engagement with a natural or prosthetic concave cup portion.

Example 12 can include, or can optionally be combined with the subject matter of one or any combination of Examples 1-11, to optionally include or use a membrane disposed between the first and second ceramic components. The membrane can be coupled to a portion of each ceramic component.

Example 13 can include, or can optionally be combined with the subject matter of one or any combination of Examples 1-12, to optionally include or use a ceramic material of each of the first and second ceramic components comprising at least one of alumina ($Al_2O_3$), zirconia ($ZrO_2$), silica ($SiO_2$), hydroxyapatite ($Ca_{10}(PO_4)_6(OH)_2$), titanium nitride (TiN), and silicon nitride ($Si_3N_4$).

Example 14 can include, or can optionally be combined with the subject matter of one or any combination of Examples 1-13, to optionally include or use the first and second ceramic portions forming a convex articulating portion of a prosthetic joint.

Example 15 can include, or can optionally be combined with the subject matter of one or any combination of Examples 1-14, to optionally include or use the first and second ceramic portions forming a cup portion of a prosthetic joint.

Example 16 can include, or can optionally be combined with the subject matter of one or any combination of Examples 1-15, to optionally include or use the first and second ceramic portions forming a portion of a prosthetic knee implant, a portion of a prosthetic finger implant, a portion of a prosthetic toe implant, a portion of a prosthetic shoulder implant, a portion of a prosthetic arm implant, a portion of a prosthetic elbow implant, a portion of a prosthetic hip implant, a portion of a prosthetic ankle implant, a portion of a prosthetic neck implant, a portion of a prosthetic spinal cord implant, or a portion of a prosthetic trauma implant.

Example 17 can include, or can optionally be combined with the subject matter of one or any combination of Examples 1-16, to include subject matter (such as an apparatus, a device, a method, or one or more means for performing acts), such as can include a method of fabricating a prosthetic construct. The subject matter can comprise forming a first ceramic component having a first surface. The first ceramic component can comprise a first ceramic material. A second ceramic component having a second surface can be formed. The second ceramic component can comprise a second ceramic material. The second surface of the second ceramic component can be disposed on the first surface of the first ceramic component. The first ceramic material and the second ceramic material can be heated. The first ceramic component and the second ceramic component can be cooled so that the second ceramic component induces a compressive stress on the first ceramic component.

Example 18 can include, or can optionally be combined with the subject matter of one or any combination of Examples 1-17, to optionally include heating the first and second ceramic components to include increasing an original size of the second ceramic component a greater relative amount than increasing an original size of the first ceramic component.

Example 19 can include, or can optionally be combined with the subject matter of one or any combination of Examples 1-18, to optionally include cooling the first and second ceramic components to include increasing a strength or toughness of the prosthetic construct, when combined, or changing a failure mode of the prosthetic construct, relative to individual strengths, toughnesses, or failure modes of the first or second ceramic component, when separate.

Example 20 can include, or can optionally be combined with the subject matter of one or any combination of Examples 1-19, to optionally include the compressive stress offsetting a use-based tensile clinical load.

Example 21 can include, or can optionally be combined with the subject matter of one or any combination of Examples 1-20, to optionally include forming the first ceramic component and forming the second ceramic component each comprising forming the ceramic components from at least one of alumina ($Al_2O_3$), zirconia ($ZrO_2$), silica ($SiO_2$), hydroxyapatite ($Ca_{10}(PO_4)_6(OH)_2$), titanium nitride (TiN), and silicon nitride ($Si_3N_4$).

Example 22 can include, or can optionally be combined with the subject matter of one or any combination of Examples 1-21, to optionally include forming the first or second ceramic component including forming a ball portion of a prosthetic joint.

Example 23 can include, or can optionally be combined with the subject matter of one or any combination of Examples 1-22, to optionally include forming the first and second ceramic component including forming a generally spherical shape having an articulating bearing surface sized and shaped for seated engagement with a natural or prosthetic concave cup portion.

Example 24 can include, or can optionally be combined with the subject matter of one or any combination of Examples 1-23, to optionally include disposing a membrane between the first ceramic component and the second ceramic component. The membrane can provide for fracture reinforcement to one or both of the first and second ceramic components.

Example 25 can include include subject matter (such as an apparatus, a device, a method, or one or more means for performing acts), a kit. The subject matter can include or can optionally be combined with the subject matter of any combination of Examples 1-24, to optionally include instructions for using a prosthetic construct.

Example 26 can include, or can optionally be combined with the subject matter of one or any combination of Examples 1-25, to include subject matter (such as an apparatus, a device, a method, or one or more means for performing acts), such as can include a prosthetic construct. The subject matter can comprise a ceramic component. A membrane can be disposed onto and bonded to at least a portion of the ceramic component. The membrane can be configured to provide fracture reinforcement to the ceramic component.

Example 27 can include, or can optionally be combined with the subject matter of one or any combination of Examples 1-26, to optionally include a second component. The membrane can be disposed between the ceramic component and the second component. The membrane can be bonded to at least a portion of each of the ceramic component and the second component.

Example 28 can include, or can optionally be combined with the subject matter of one or any combination of Examples 1-27, to optionally include the ceramic component including a first ceramic component and a second ceramic component. The second ceramic component can include a different ceramic material or can have a different material property than the first ceramic component.

Example 29 can include, or can optionally be combined with the subject matter of one or any combination of Examples 1-28, to optionally include the second ceramic component inducing a compressive stress on the first ceramic component.

Example 30 can include, or can optionally be combined with the subject matter of one or any combination of Examples 1-29, to optionally include the ceramic component being in the form of a ball portion of a prosthetic joint.

Example 31 can include, or can optionally be combined with the subject matter of one or any combination of Examples 1-30, to optionally include the ceramic component being in the form of a cup portion of a prosthetic joint.

Example 32 can include subject matter (such as an apparatus, a device, a method, or one or more means for performing acts), such as can include a kit. The subject matter can include or can optionally be combined with the subject matter of any combination of Examples 1-31, to optionally include instructions for using the prosthetic construct.

Example 33 can include, or can optionally be combined with the subject matter of one or any combination of Examples 1-32, to include subject matter (such as an apparatus, a device, a method, or one or more means for performing acts), such as can include a method of fabricating a prosthetic construct. The subject matter can comprise forming a first component having a first surface. The first component can comprise a ceramic material. A second component having a second surface can be formed. A membrane can be disposed between the first component and the second component so that the membrane is between the first surface and the second surface. The membrane can be bonded to at least a portion of the first component and to at least a portion of the second component. The membrane can be configured to provide for fracture reinforcement to one or both of the first component and the second component.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A prosthetic construct configured to replace a portion of a bone joint, the prosthetic construct comprising:
    a first ceramic component having an outer surface defining a body of the construct shaped for articulation with a corresponding natural or prosthetic joint construct, the first ceramic component comprising a first ceramic material and the outer surface is formed of the first ceramic material; and
    a second ceramic component having an outer joint articulation surface and an inner surface disposed on the outer surface of the first ceramic component, the second ceramic component comprising a second ceramic material and the inner surface is formed of the second ceramic material, wherein the second ceramic material of the second ceramic component includes a higher coefficient of thermal expansion than the first ceramic material of the first ceramic component, and wherein the higher coefficient of thermal expansion of the second ceramic material of the second ceramic component causes the second ceramic component to exert a compressive force on the first ceramic component, independent of external forces on the prosthetic construct.

2. The prosthetic construct of claim 1, wherein the first and second ceramic components, when combined, increase a strength or toughness of the prosthetic construct or change a failure mode of the prosthetic construct, relative to individual strengths, toughnesses, or failure modes of the first or second ceramic component, when separate.

3. The prosthetic construct of claim 1, wherein the compressive force is exerted in generally the same direction as an expected clinical load to be exerted on the prosthetic construct.

4. The prosthetic construct of claim 1, wherein the second ceramic material comprises a different ceramic material than the first ceramic material.

5. The prosthetic construct of claim 1, wherein the inner surface of the second ceramic component is sized and shaped to receive the outer surface of the first ceramic component.

6. The prosthetic construct of claim 1, wherein each of the first and second ceramic components include a generally spherical shape, and an outer surface diameter of the generally spherical shape of the first ceramic component is less than an outer surface diameter of the generally spherical shape of the second ceramic component.

7. The prosthetic construct of claim 1, wherein the compressive force is configured to counteract use-based load tensile clinical load.

8. The prosthetic construct of claim 1, wherein the second ceramic component is sized and shaped to substantially surround the first ceramic component.

9. The prosthetic construct of claim 1, wherein the outer joint articulation surface of the second ceramic component includes a convex portion defining an articulating bearing surface sized and shaped for seated engagement with a natural or prosthetic concave cup portion of the corresponding joint construct.

10. The prosthetic construct of claim 1, further comprising a membrane disposed between the first and second ceramic components, the membrane coupled to a portion of each ceramic component.

11. The prosthetic construct of claim 1, wherein a ceramic material of each of the first and second ceramic components comprises at least one of alumina ($Al_2O_3$), zirconia ($ZrO_2$), silica ($SiO_2$), hydroxyapatite ($Ca_{10}(PO_4)_6(OH)_2$), titanium nitride (TiN), and silicon nitride ($Si_3N_4$).

12. The prosthetic construct of claim 1, wherein the prosthetic construct includes at least a portion of a hip implant.

13. The prosthetic construct of claim 1, wherein the prosthetic construct includes at least a portion of a distal femoral implant.

* * * * *